US008716016B2

(12) United States Patent
Coussens et al.

(10) Patent No.: US 8,716,016 B2
(45) Date of Patent: May 6, 2014

(54) IMMORTAL AVIAN CELL LINE AND METHODS OF USE

(75) Inventors: Paul Michael Coussens, Belaire, MI (US); Kristen Ann Smith Pabst, East Lansing, MI (US); Patty Sue Dickerson-Weber, St. Johns, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 182 days.

(21) Appl. No.: 12/989,261

(22) PCT Filed: Apr. 23, 2009

(86) PCT No.: PCT/US2009/041548
§ 371 (c)(1), (2), (4) Date: Apr. 15, 2011

(87) PCT Pub. No.: WO2009/132195
PCT Pub. Date: Oct. 29, 2009

(65) Prior Publication Data

US 2011/0182931 A1 Jul. 28, 2011

Related U.S. Application Data

(60) Provisional application No. 61/047,123, filed on Apr. 23, 2008.

(51) Int. Cl.
*C12N 15/85* (2006.01)
*C12N 15/86* (2006.01)
*C12P 21/00* (2006.01)
*C12N 7/00* (2006.01)
*A61K 35/56* (2006.01)

(52) U.S. Cl.
CPC .............. *C12N 7/00* (2013.01); *C12N 2510/02* (2013.01); *C12N 2510/04* (2013.01); *C12N 2710/24151* (2013.01); *C12N 2500/98* (2013.01); *C12N 2506/02* (2013.01); *A61K 35/57* (2013.01)
USPC ........ 435/325; 435/70.1; 435/1.1; 435/283.1; 435/405; 435/235.1

(58) Field of Classification Search
CPC .. C12N 2510/02; C12N 2510/04; C12N 7/00; C12N 2710/24151; C12N 2500/80; C12N 2500/98; C12N 2506/02; A61K 35/57
USPC ................................................ 435/325, 70.1
See application file for complete search history.

(56) References Cited

U.S. PATENT DOCUMENTS 5,827,738 A * 10/1998 Coussens et al. ............. 435/349
5,833,980 A * 11/1998 Coussens et al. .......... 424/93.21
5,866,117 A * 2/1999 Coussens et al. .......... 424/93.21
5,874,303 A * 2/1999 Coussens et al. ............. 435/349
5,989,805 A 11/1999 Reilly et al.
2004/0058441 A1 3/2004 Pain et al.
2006/0063261 A1 3/2006 Pau et al.
2006/0094104 A1 5/2006 Grillberger et al.
2007/0178120 A1* 8/2007 Morrison et al. .......... 424/214.1
2009/0239297 A1 9/2009 Pain et al.
2010/0221825 A1 9/2010 Pain et al.
2011/0294209 A1 12/2011 Pain et al.
2012/0058539 A1* 3/2012 Sene et al. .................... 435/238
2012/0070893 A9 3/2012 Pain et al.
2012/0207785 A1* 8/2012 Fabry et al. ................ 424/209.1
2012/0276614 A1* 11/2012 Malarme et al. .............. 435/236
2013/0084620 A1* 4/2013 Malarme et al. .............. 435/239

FOREIGN PATENT DOCUMENTS

WO WO 03076601 A1 * 9/2003
WO WO-2009132195 A1 10/2009

OTHER PUBLICATIONS

Coussens PM, Smith KA, Weber PS, Colvin CJ. Immortalized chick embryo cell line adapted to serum-free growth conditions and capable of replicating human and reassortant H5N1 influenza strains for vaccine production. Vaccine. Nov. 3, 2011;29(47):8661-8. Epub Sep. 10, 2011.*
Merten OW, Kallel H, Manuguerra JC, Tardy-Panit M, Crainic R, Delpeyroux F, Van der Werf S, Perrin P. The new medium MDSS2N, free of any animal protein supports cell growth and production of various viruses. Cytotechnology. Jul. 1999;30(1-3):191-201.*
Kalbfuss B, Genzel Y, Wolff M, Zimmermann A, Morenweiser R, Reichl U. Harvesting and concentration of human influenza A virus produced in serum-free mammalian cell culture for the production of vaccines. Biotechnol Bioeng. May 1, 2007;97(1):73-85.*
Smith KA, Colvin CJ, Weber PS, Spatz SJ, Coussens PM. High titer growth of human and avian influenza viruses in an immortalized chick embryo cell line without the need for exogenous proteases. Vaccine. Jul. 4, 2008;26(29-30):3778-82. Epub May 8, 2008.*
Ignjatovic J, Bagust TJ. Variation in susceptibility to avian sarcoma viruses and expression of endogenous avian leukosis virus antigens in specific pathogen-free chicken lines. J Gen Virol. Aug. 1985;66 ( Pt 8):1723-31.*
Li X, Qin Q, Zhang N, Zhu W, Zhang J, Wang H, Miao L, Zhang H. A new insect cell line from pupal ovary of *Spodoptera exigua* established by stimulation with N-methyl-N'-nitro-N-nitrosoguanidine (MNNG). In Vitro Cell Dev Biol Anim. May 2012;48(5):271-5. Epub May 2, 2012.*
Figure adapted from ICTV Master Species List, ver. 1, 2012; Antiviral InteliStrat Inc. “Simplified taxonomy of main viruses infecting humans.” Downloaded Mar. 4, 2013.*
Matthews et al., 1987, AIDS Research and Human Retroviruses, 3(1):197-206.*

(Continued)

*Primary Examiner* — Benjamin P Blumel
*Assistant Examiner* — Rachel Gill
(74) *Attorney, Agent, or Firm* — Schwegman, Lundberg & Woessner, P.A.

(57) ABSTRACT

A avian cell line that supports replication of animal or human viruses, which cell line is adapted to animal-product free growth. The cell line is useful for propagating a virus suitable as a live or a killed vaccine and for virus isolation and diagnostic assays.

20 Claims, 5 Drawing Sheets

(56) References Cited

OTHER PUBLICATIONS

Whitley RJ. Herpesviruses. In: Baron S, editor. Medical Microbiology. 4th edition. Galveston (TX): University of Texas Medical Branch at Galveston; 1996. Chapter 68. Available from: http://www.ncbi.nlm.nih.gov/books/NBK8157/.*

Deng X, Gao Y, Gao H, Qi X, Cheng Y, Wang X, Wang X. Antigenic structure analysis of VP3 of infectious bursal disease virus. Virus Res. Oct. 2007;129(1):35-42. Epub Jun. 27, 2007.*

Cao W, Henry MD, Borrow P, Yamada H, Elder JH, Ravkov EV, Nichol ST, Compans RW, Campbell KP, Oldstone MB. Identification of alpha-dystroglycan as a receptor for lymphocytic choriomeningitis virus and Lassa fever virus. Science. Dec. 11, 1998;282(5396):2079-81.*

Urata S, Yasuda J. Molecular mechanism of arenavirus assembly and budding. Viruses. Oct. 10, 2012;4(10):2049-79.*

Kraft V, Tischer I. Cell cycle-dependent multiplication of avian adenoviruses in chicken embryo fibroblasts. Arch Virol. 1978;57(3):243-54.*

Chambers P, Samson AC. Non-structural proteins in Newcastle disease virus-infected cells. J Gen Virol. Jan. 1982;58 Pt 1:1-12.*

Dar A, Munir S, Vishwanathan S, Manuja A, Griebel P, Tikoo S, Townsend H, Potter A, Kapur V, Babiuk LA. Transcriptional analysis of avian embryonic tissues following infection with avian infectious bronchitis virus. Virus Res. Jun. 2005;110(1-2):41-55.*

Freire MS, Mann GF, Marchevsky RS, Yamamura AM, Almeida LF, Jabor AV, Malachias JM, Coutinho ES, Galler R. Production of yellow fever 17DD vaccine virus in primary culture of chicken embryo fibroblasts: yields, thermo and genetic stability, attenuation and immunogenicity. Vaccine. Mar. 31, 2005;23(19):2501-12.*

Ben-Nathan D, Lustig S. Production of Marek's disease vaccine. Adv Biotechnol Processes. 1990;14:347-65.*

Liu Q, Hobom G. Agnoprotein-1a of avian polyomavirus budgerigar fledgling disease virus: identification of phosphorylation sites and functional importance in the virus life-cycle. J Gen Virol. Feb. 2000;81(Pt 2):359-67.*

Gilbert PA, Comanita L, Barrett J, Peters A, Szabat M, McFadden G, Dekaban GA. Current Status for High Titre Poxvirus Stock Preparation in CEF Under Serum-Free Medium Conditions: Implication for Vaccine Development. Cytotechnology. Jun. 2005;48(1-3):79-88.*

Meng S, Jiang K, Zhang X, Zhang M, Zhou Z, Hu M, Yang R, Sun C, Wu Y. Avian reovirus triggers autophagy in primary chicken fibroblast cells and Vero cells to promote virus production. Arch Virol. Apr. 2012;157(4):661-8. Epub Jan. 13, 2012.*

Maas R, van Zoelen D, Oei H, Claassen I. Replacement of primary chicken embryonic fibroblasts (CEF) by the DF-1 cell line for detection of avian leucosis viruses. Biologicals. Sep. 2006;34(3):177-81. Epub Oct. 28, 2005.*

Song KD, Lillehoj HS, Choi KD, Zarlenga D, Han JY. Expression and functional characterization of recombinant chicken interferon-gamma. Vet Immunol Immunopathol. Sep. 19, 1997;58(3-4):321-33.*

Schlesinger RW. Sindbis virus replication in vertebrate and mosquito cells: an interpretation. Med Biol. Oct. 1975;53(5):295-301.*

Ogura H, Fujiwara T, Namba M. Establishment of two chick embryo fibroblastic cell lines. Gann. May 1984;75(5):410-4.*

"International Application Serial No. PCT/US2009/041548, International Search Report and Written Opinion mailed Jun. 18, 2009", 6 pgs.

Pharmaceutical News, HepaLife's PBS-1 Cells for Influenza Vaccine Production Prove Superior at International Conference, Boston (Business Wire) Jun. 25, 2007. [Retrieved on May 23, 2009]. Retrieved from the Internet <URL: http://www.drugs.com/clinical_trials/hepalife-s-pbs-1-cells-influenza-vaccine-production-prove-superior-international-conference-1408.html>, p. 2, para 1 and 4.

Abujoub, A., et al., "Development of a Sustainable Chick Cell Line Infected with Marek's Disease Virus", Virology, 214(2), (1995), 514-9.

Bardiya, N., et al., "Influenza vaccines: recent advances in production technologies", Appl Microbiol Biotechnol., 67(3), (May 2005), 299-305.

Genzel, Y., et al., "Serum-free influenza virus production avoiding washing steps and medium exchange in large-scale microcarrier culture", Vaccine, 24(16), (Apr. 12, 2006), 3261-72.

Gos, M., et al., "Cellular quiescence induced by contact inhibition or serum withdrawal in C3H10T1/2 cells", Cell Prolif., 38(2), (Apr. 2005), 107-16.

Kistner, O., et al., "Development of a mammalian cell (Vero) derived candidate influenza virus vaccine", Vaccine, 16(9-10), (May-Jun. 1998), 960-8.

Lavrentieva, I. N, et al., "Characterization of the reproduction of influenza A epidemic viruses in cell cultures", Acta Virol., 30(2), (Mar. 1986), 137-42.

Ogura, H., et al., "Establishment and characterization of a virus-free chick cell line", Acta Med Okayama, 41(3), (Jun. 1987), 141-3.

Pau, M. G, et al., "The human cell line PER.C6 provides a new manufacturing system for the production of influenza vaccines", Vaccine, 19(17-19), (Mar. 21, 2001), 2716-21.

Pochampally, R. R, et al., "Serum deprivation of human marrow stromal cells (hMSCs) selects for a subpopulation of early progenitor cells with enhanced expression of OCT-4 and other embryonic genes", Blood, 103(5), (Mar. 1, 2004), 1647-52.

Szretter, K. J, et al., "Influenza: propagation, quantification, and storage", Curr Protoc Microbiol., (Dec. 2006), Chapter 15:Unit 15G.1.

Tree, J. A, et al., "Comparison of large-scale mammalian cell culture systems with egg culture for the production of influenza virus A vaccine strains", Vaccine, 19(25-26), (May 14, 2001), 3444-50.

Wood, J. M, et al., "Preparation of vaccines against H5N1 influenza", Vaccine, 20(Suppl 2), (May 15, 2002), S84-7.

* cited by examiner

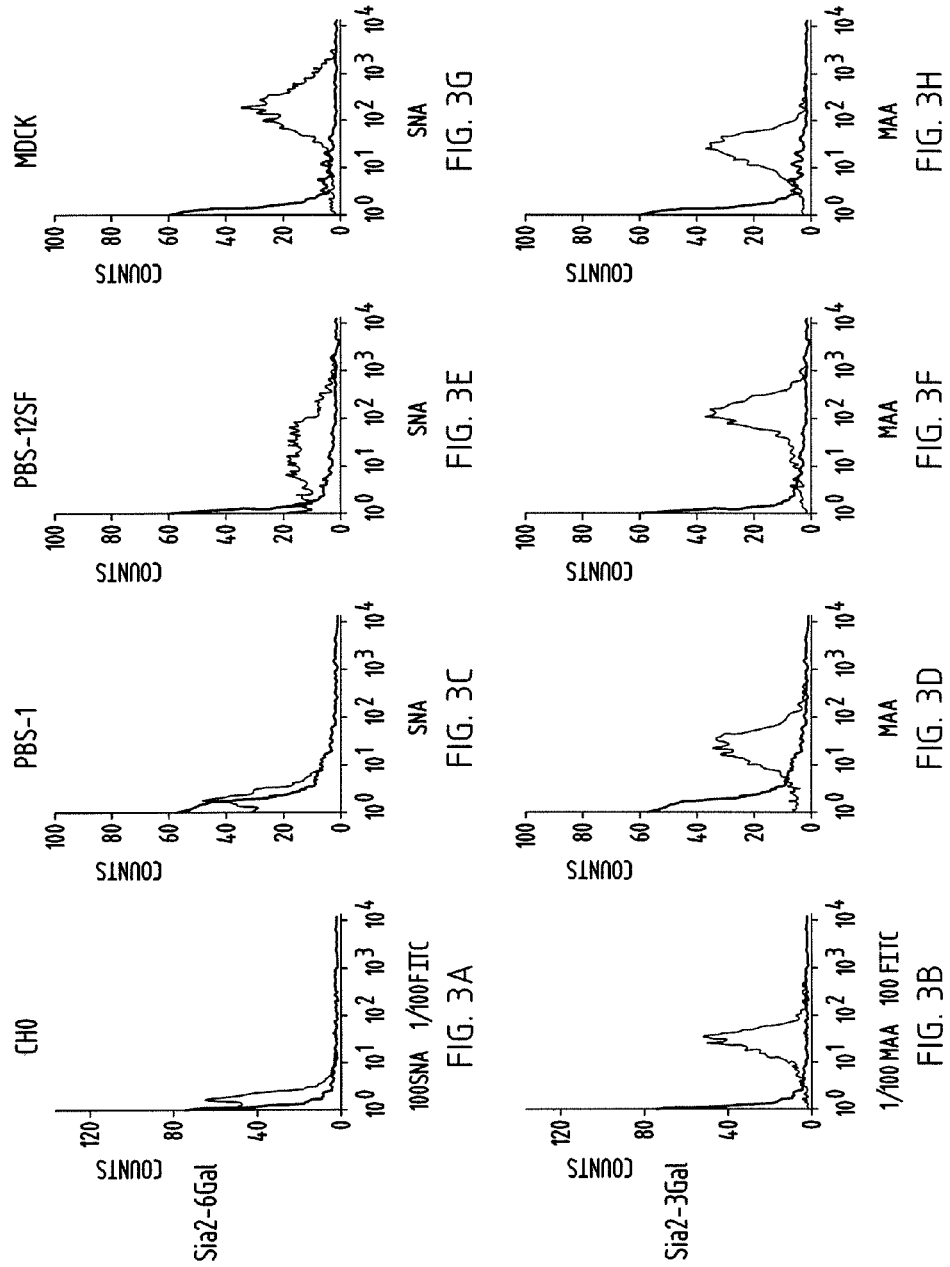

VNH5N1-PR8/CDC-RG

| Cell line | Average titer | Standard deviation |
|---|---|---|
| MDCK | 4.38 | 1.93 |
| PBS-12SF | 5.64 | 1.27 |
| PBS-1 | 5.78 | 1.12 |

Anhui/01/2005-PR8 IBCDC G-5

| Cell line | Average titer | Standard deviation |
|---|---|---|
| MDCK | 6.10 | 2.49 |
| PBS-12SF | 5.81 | 1.76 |
| PBS-1 | 4.88 | 2.68 |

A/NewCaledonia/20/1999

| Cell line | Average titer | Standard deviation |
|---|---|---|
| MDCK | 5.01 | 2.08 |
| PBS-12SF | 7.10 | 1.69 |
| PBS-1 | 6.68 | 1.65 |

A/Wisconsin/67/2005

| Cell line | Average titer | Standard deviation |
|---|---|---|
| MDCK | 2.61 | 3.72 |
| PBS-12SF | 5.16 | 1.06 |
| PBS-1 | 6.41 | 2.75 |

Passage Number

▲ PBS-1   ■ PBS-12SF   ● MDCK

IMMORTAL AVIAN CELL LINE AND METHODS OF USE

CROSS-REFERENCE TO RELATED APPLICATIONS

This application is a National Stage of PCT/US2009/041548, filed Apr. 23, 2009, which claims priority to U.S. Provisional Patent Application No. 61/047,123 filed Apr. 23, 2008.

FIELD OF THE INVENTION

This invention is in the field of cell biology and, more specifically, relates to an isolated avian cell line and methods of using the cell line for propagating viruses, for virus isolation, and for diagnostic assays.

BACKGROUND OF THE INVENTION

The following viruses are examples of viruses that are propagated in embryonated eggs or in primary cultures of chicken embryo fibroblasts prepared from embryonated eggs: avian influenza virus, avian reovirus, fowlpox virus, psittacine herpesvirus (Pachecco's herpesvirus), swine influenza virus, equine influenza virus, Newcastle disease virus, falcon herpesvirus, pigeon herpesvirus, infectious bursal disease virus, infectious bronchitis virus, Marek's disease virus, turkey herpesvirus, chicken anemia virus, avian encephalomyelitis virus, pigeon pox virus, canary pox virus, quail pox virus, avian polyomavirus types I and II, and avian adenovirus types I, II, and III. Further, following are examples of human viruses that are propagated in embryonated eggs or in primary avian cell cultures: Influenza A and Influenza B viruses, West Nile virus, yellow fever virus, Chikungunya virus, Dengue fever virus, and most encephalitis viruses.

Detection of any one of the above-identified viruses as the etiological agent for a diseased animal or human can be determined by serological based assays or unequivocally by virus isolation (VI) diagnostic assays. For many of these viruses, live or killed vaccines are available to protect the animal or human from infection by the aforementioned viruses.

Current influenza vaccine production technology is largely restricted to growing viruses in embryonated chicken eggs, often requiring one to two eggs per dose [29,30]. This production scheme thus requires that hundreds of millions of "clean" embryonated eggs are available each year to meet the demand for influenza vaccines. In addition, this scheme requires significant downstream processing to purify virus away from egg components and is subject to significant loss of product if the eggs used are found to be contaminated with exogenous agents, such as *Salmonella* spp. From selection of vaccine viruses (to be included in any given year's vaccine) to actual production can take as long as six to nine months. Many scientists and vaccine experts have expressed concern that this is far too long in the face of a potential pandemic [21, 29, 30]. There are also concerns that individuals who are allergic to eggs may experience adverse reactions to egg-derived vaccines.

Because of safety and consistency issues with egg-derived influenza vaccines, there has recently been a push from both regulatory agencies and major vaccine manufacturers to adopt a continuous cell culture-based influenza vaccine production system (FDA, 2001). The recent emergence of potentially pandemic influenza viruses, such as high pathogenicity H5N1 strains has also highlighted deficiencies in the ability of current manufacturing systems to rapidly respond to a pandemic [21, 30]. While influenza viruses generally grow efficiently on primary chick kidney cells [11, 15], this system would be subject to many of the same concerns and issues surrounding egg-derived vaccines, particularly the potential presence of harmful contaminating pathogens.

Thus, a well-characterized continuous cell line that can be used to establish a master cell bank free of exogenous pathogens is valuable. The "PBS-1" cell line is one such known cell line. PBS-1 is an immortalized chick embryo cell line that is capable of growing viruses to high titers. Viruses grown in PBS-1 cells are released into the culture fluid without the need for exogenous proteases, thus simplifying downstream processing. PBS-1 cells are free of any exogenous agents, are non-tumorigenic, and are readily adaptable to a variety of culture conditions, including growth on microcarrier beads. The PBS-1 cell line, and methods of use of this cell line, are disclosed in five U.S. Pat. Nos. 5,827,738; 5,833,980; 5,874,303; 5,866,117; and 5,989,805, all of which patents are incorporated herein as if fully set forth. Due to its embryonic nature, the PBS-1 cell line has been shown to be susceptible to a wide range of viruses.

A cell line that adapts to serum free conditions shows advantages in the vaccine production process. The high protein concentrations present in culture media enriched with serum increases the complexity of product purification. High lot-to-lot variation of serum can be found because serum is poorly defined. Additionally, another critical aspect of using serum involves a high risk of contamination by viruses, mycoplasma, and prions [5]. Washing steps and medium exchange could be reduced if serum-free conditions are applied which can also reduce the risk of contamination and increase productivity.

Currently, there are three continuous cells lines which meet regulatory requirements and have been shown to successfully replicate influenza A and B viruses. These cells are Madin-Darby canine kidney (MDCK) cells [28], African green monkey kidney cells (Vero) [14], and human fetal retinoblast cells (PER.C6) [19]. All three of these cell lines have been adapted to grow in serum free media [14, 19, 28].

The PBS-1 cell line requires serum or animal product (e.g., bovine serum) for growth. As such, the utility of PBS-1 for manufacturing human vaccines is limited by the potential for contaminating elements such as bovine spongiform encephalopathy (BSE), a progressive neurological disease that is fatal to cattle and has been associated with variant human Creutzfeld-Jacob syndrome. Accordingly, it is desirable to have a cell line derived from the PBS-1 cell line that is adapted for growth in serum-free or animal-product free conditions.

SUMMARY OF THE INVENTION

The present invention includes an isolated cell line named "PBS-12 SF" that was established from the PBS-1 cell line. More specifically, the present invention includes the PBS-12 SF immortalized chick embryo cell line deposited with the American Type Culture Collection, 10801 University Blvd., Manassas, Va. 20110-2209, a recognized public depository for strains of microorganisms, under the provisions of the Budapest Treaty, as Patent Deposit Designation PTA-8565, having been deposited on Aug. 2, 2007. The cell line will be irrevocably available from the ATCC® (American Type Culture Collection) for the life of the patent.

According to one embodiment of the invention, there is provided a cell that is a clone, derivative, mutant, and/or transfectant of the cell line designated ATCC®-PTA-8565 (American Type Culture Collection), wherein the cell upon culture grows continuously and retains the identifying characteristics of the cell line designated ATCC®-PTA 8565 (American Type Culture Collection).

The PBS-12 SF cell line is capable of growth in serum-free or animal-product free conditions. PBS-12 SF cells have developed Sia2-6Gal-containing receptors in addition to Sia2-3Gal receptors. Additionally, this new cell line has been shown to successfully replicate human and reassortant influenza virus at titers comparable to MDCK, Vero, and CEK cells. Unlike Vero and MDCK cells, PBS-12SF cells do not require TPCK-treated trypsin for efficient growth of the influenza viruses on the cells, which can simplify downstream processing in vaccine production. Further, the PBS-12 SF cell line can be used for (a) propagating human or animal viruses for use in vaccines, (b) virus isolation assays, and (c) diagnostic assays.

The present invention also includes (a) an immortalized, contact-inhibited, non-malignantly transformed chicken cell line, comprising chick embryo cells (CEC) that are adapted to serum-free growth or animal-product-free growth; and (b) a sustainable chicken cell line which replicates continuously in cell culture, and is contact-inhibited, chicken helper factor (Chf) negative, and virus-free, comprising CEC that are adapted to animal-product-free growth.

Any of the above-mentioned inventive cell lines (or a host cell from the cell lines) may be infected with a virus, and the infection may be maintained as a non-lytic infection or converted to a lytic infection. Further, (a) the virus may be selected from the group of virus families consisting of Adenoviridae, Arenaviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, Togaviridae; (b) the virus may be capable of use in the preparation of a virus vaccine; (c) the virus may be recombinant, such as where one or more foreign genes have been inserted into or deleted from the virus, or where the entire viral genome is contained within a plasmid or plasmids; or (d) the cell line may produce infectious virus when the cell culture is sub-confluent or confluent. Also, for any of the above-mentioned inventive cell lines, the cells may be treated with N-methyl-N1-nitro-N-nitrosoguanidine (MNNG) to render the cell line continuously replicating and contact-inhibited without malignantly transforming the cells; and the cell line may be capable of growing in a suspension.

The present invention also includes a method of producing a vaccine including the steps of providing any of the above-mentioned inventive cell lines; infecting the cell line with a virus, or transfecting the cell line with a productive clone or clones containing a viral genome, or transfecting the cell line with a plasmid or plasmids containing a viral genome; cultivating the infected or transfected cell line; and harvesting the virus from the cell line. The virus may be selected from the group of virus families consisting of Adenoviridae, Arenaviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, Togaviridae. Further, the method may include the step of inactivating the virus. Another invention includes the method of administering a vaccine to an animal or a human, comprising providing the vaccine produced according to the method described in this paragraph; and inoculating an animal or human with the virus.

A further invention includes a vaccine in dosage unit form comprising any of the above-mentioned inventive cell lines that has been infected with a virus. With this vaccine, the virus may be selected from the group of virus families consisting of Adenoviridae, Arenaviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, Togaviridae; and the vaccine may be an animal or a human vaccine.

A further method includes identifying a virus, comprising: (a) providing one of the above-mentioned inventive cell lines; (b) infecting said cell line with a virus; (c) cultivating the infected cell line to produce the virus; (d) reacting said infected cell line with an antibody or other reagent specific for the virus; and (e) visualizing infected cells reacted with the antibody or other reagent. With this method, the virus may be selected from the group consisting of Adenoviridae, Arenaviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, Togaviridae. The cell line used with this method may be ATCC® (American Type Culture Collection) number PTA-8565.

BRIEF DESCRIPTION OF THE DRAWINGS

The foregoing summary, as well as the following detailed description of the invention, will be better understood when read in conjunction with the appended drawings. For the purpose of illustrating the invention, certain embodiment(s) are shown in the drawings. It should be understood, however, that the invention is not limited to the precise arrangements and instrumentalities shown. Drawings are not necessarily to scale. Certain features of the invention may be exaggerated in scale or shown in schematic form in the interest of clarity and conciseness.

FIGS. 3A-3H are graphs of the results of flow-cytometric analysis for influenza virus receptors on PBS-1, PBS-12SF, MDCK, and CHO cells. These cells were analyzed using a digoxigenin glycan differentiation kit. The cells were incubated for 1 hr at room temperature with DIG-labeled lectins *Sambucus nigra* agglutinin (SNA) (specific for Sia2-6Gal) or *Maackia amurensis* agglutinin (MAA) (specific for Sia2-3Gal). The cells were then incubated with anti-digoxigenin-fluorescein Fab fragments and then subject to flow-cytometric analysis. PBS-1 cells after MAA binding (FIG. 3D); PBS-1 cells after SNA binding (FIG. 3C); PBS12-SF cells after MAA binding (FIG. 3F); PBS12-SF cells after SNA binding (FIG. 3E); MDCK cells after MAA binding (FIG. 3H); MDCK cells after SNA binding (FIG. 3G); CHO cells after MAA binding (FIG. 3B); and CHO cells after SNA binding (FIG. 3A). The controls for PBS-1, PBS-12SF, MDCK, and CHO were populations of cells that were only stained with anti-digoxigenin-fluorescein Fab fragments, which are the unshaded profiles.

FIG. 4 shows growth titers for influenza viruses adapted to MDCK, PBS-12SF, and PBS-1 cells, which were all supplemented with 1.0 µg/ml trypsin. Reassortant strains VNH5N1-PR8/CDC-RG and Anhui/01/2005-PR8 IBCDC RG-5 and two human influenza strains A/NewCaledonia/20/1999 (H1N1) and A/Wisconsin/67/2005 (H3N2) were tested. The virus strains were infected onto the cells at an MOI of 0.1. Titration of infectious virus was performed on MDCK cells for the first two passages. Starting on the third passage, the titrations were performed on the corresponding cell line in which the virus was infected. After each passage, supernatants from each infected culture were reinfected onto the host cells at an MOI of 0.1. The log 10TCID50/ml titers were plotted after each passage. Additionally, the average growth titer of all passages and standard deviation were calculated for the supernatants of each cell line.

FIG. 5 shows hemagglutination titers for influenza viruses adapted to MDCK, PBS-12SF, and PBS-1 cells, which were all supplemented with 1.0 μg/ml trypsin. Reassortant strains VNH5N1-PR8/CDC-RG and Anhui/01/2005-PR8 IBCDC RG-5 and two human influenza strains A/NewCaledonia/20/1999 (H1N1) and A/Wisconsin/67/2005 (H3N2) were tested. The virus strains were infected onto the cells at an MOI of 0.1. After each passage, supernatants from each infected culture were reinfected onto the host cells at an MOI of 0.1. The HAU/50 μl values were calculated after each passage. This was performed by serially diluting 50 μl of culture supernatants 2-fold with PBS in V-bottom plates. Subsequently, 50 μl of 1% chicken red blood cells were added to each well. The plates were incubated for 1 hr and the HA patterns were determined visually.

DETAILED DESCRIPTION OF THE PREFERRED EMBODIMENTS

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, and from the claims. The preferred embodiments of the present invention may be understood more readily by reference to the following detailed description of the specific embodiments and the Examples included hereafter.

In this specification and the appended claims, the singular forms "a," "an" and "the" include plural reference unless the context clearly dictates otherwise.

The term "cell" is used in its usual biological sense, and does not refer to an entire multicellular organism. The cell can, for example, be in vitro, e.g., in cell culture.

The term "host cell" includes an individual cell or cell culture which can be or has been a recipient of any virus or recombinant vector(s). Host cells include progeny of a single host cell, and the progeny may not necessarily be completely identical (in morphology or in total DNA complement) to the original parent cell due to natural, accidental, or deliberate mutation and/or change. A host cell includes cells infected or tranfected with a virus or recombinant vector.

As used herein the term "isolated," in the context of a subject isolated cell, refers to a cell that is in an environment different from that in which the cell naturally occurs. As used herein, the term "immortal cell line" refers to a cell line that is immortalized, e.g., under suitable in vitro culture conditions, the cell line divides virtually indefinitely. Isolated cells also include "host cells."

The term "recombinant" when used with reference, e.g., to a cell, nucleic acid, vector, virus indicates that the cell, nucleic acid, virus, or vector has been modified by the introduction of a heterologous nucleic acid or by the alteration of a native nucleic acid, or that the cell, nucleic acid, virus, or vector is derived from a cell, nucleic acid, virus, or vector so modified. Thus, for example, recombinant cells express genes and proteins that are not found within the native (non-recombinant) form of the cell or express native genes and proteins that are otherwise abnormally expressed, under expressed or not expressed at all.

The progenitor cell line to PBS-1 cells were derived in 1984-87 at the Department of Virology, Cancer Institute, Okyama University Medical School, Okyama, Japan by Hajime Ogura and Tazuko Fujiwara and designated "CHCC-OU2" [18]. Source tissues for CHCC-OU2 cells were 11-day old line C/CE chick embryos. This chicken line, obtained from the Foundation for Microbial Diseases of Osaka University, Kanonji, Japan, was chick helper factor free and specific pathogen free. Primary cells were passed once and treated with N-methyl-N'-nitro-N-nitrosoguanidine (MNNG) [18]. No viruses or exogenous DNA were used in the immortalization phase of CHCC-OU2 cells. Following treatment with MNNG, cells exhibited exponential growth to passage 25, with cessation of growth by passage 28. Cells were continuously passed to new flasks and growth medium until passage 35 when an apparently age-released exponential growth began. Cells were held in continuous culture for 300 passages during the subsequent 3 years and continued to exhibit exponential growth. During this time, cells were always maintained in medium consisting of minimal essential medium (Nissui, Japan), supplemented with 1% heat-inactivated chicken serum (Flow Laboratories, USA), 5% calf serum (Difco Laboratories, USA) and 10% tryptose phosphate broth (Difco Laboratories, USA) at 41° C. [18].

In 1988, cells from the 300th passage were transferred by overnight courier to the USDA Avian Oncology and Diseases Laboratory in East Lansing, Mich., USA, as frozen stocks on dry ice. CHCC-OU2 cells were expanded to passage 3 after arrival (total passage from origin 303) and cryogenically stored in liquid nitrogen.

In 1993, cryogenically stored CHCC-OU2 cells were obtained by the Molecular Pathogenesis Laboratory (MPL), Michigan State University in East Lansing, Mich., and thawed into culture medium consisting of Leibovitz L 15-McCoy 5A (LM, 1:1) supplemented with 10% fetal bovine serum and 2% tryptose phosphate broth. Cells were passed and expanded under these conditions to passage level 3 (total passage from origin 306) and cryogenically stored in liquid nitrogen. CHCC-OU2 cells were subsequently developed as a continuous cell line capable of growing Marek's disease virus in both latent and infective states [1, 2].

In 1996, representative cultures of CHCC-OU2 cells were tested for presence of various adventitious agents that could have come from the species of origin or culture in bovine products (Table 1).

TABLE 1

Figure 1:
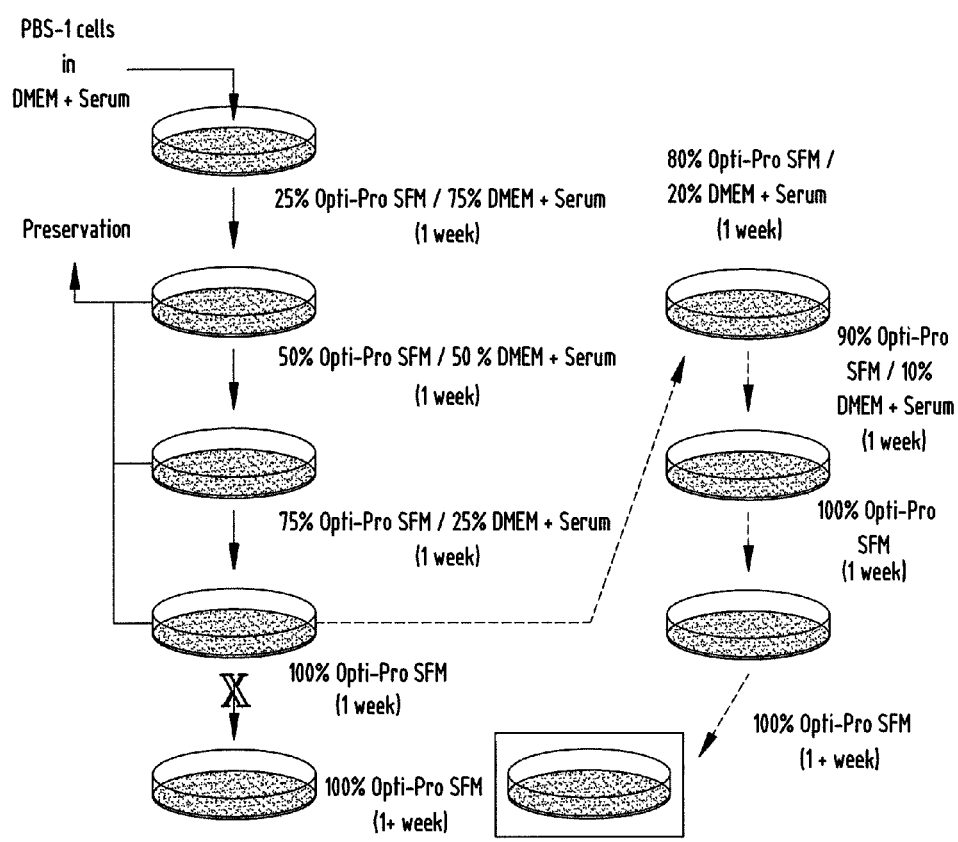
FIG. 1 is a schematic diagram of the protocol for adapting PBS-1 cells to serum free growth.

Initial adventitious agents testing of PBS-1 Progenitor cells

| Agent | Result |
| --- | --- |
| Avian Adenovirus: Group I (CELO) | Negative |
| Avian Adenovirus: Group II (HEV) | Negative |
| Avian Adenovirus: Group III (EDS-76) | Negative |
| Avian Encephalomyelitis | Negative |
| Avian Influenza - Type A | Negative |
| Avian Nephritis | Negative |
| Avian Reovirus | Negative |
| Avian Rhinotracheitis | Negative |
| Avian Rotavirus (Group A) | Negative |
| Chicken Anemia Virus | Negative |
| Fowl Pox | Negative |
| Infectious Bronchitis | Negative |
| Infectious Bursal Disease | Negative |
| Infectious Laryngotracheitis | Negative |
| Lymphoid Leukosis (antibodies) | Negative |
| Lymphoid Leukosis Virus (antigen) | Negative |
| Marek's Disease Virus | Negative |
| *Mycoplasma gallisepticum* | Negative |
| *Mycoplasma synoviae* | Negative |
| Newcastle Disease Virus | Negative |
| Paramyxovirus (Type 2) | Negative |
| Reticuloendotheliosis Virus | Negative |
| *Salmonella* | Negative |

Based on this testing, the cells were deemed free of common adventitious agents due to tissue source and to cultivation to this date. Cells were also tested for tumorigenicity in newly hatched chicks (wing web) and nude mice and were found to be non-tumorigenic in either species. Subsequent work demonstrated the ability of CHCC-OU2 cells to grow a number of different viruses, including Newcastles disease virus, Reovirus, and several strains of influenza virus.

In 1999, cryogenically stored CHCC-OU2 cells at passage 3 (total passage from origin 306) were thawed into Dulbecco's Modified Eagles Medium (DMEM) supplemented with 10% fetal bovine serum (complete DMEM). Cells were re-tested for several adventitious agents, including avian leucosis virus (ALV). Cells found to be free of ALV were expanded through 3-4 passages and again stored under liquid nitrogen (total passage from origin 309-310).

In August 2006, CHCC-OU2 cells were thawed into DMEM supplemented with 10% certified fetal bovine serum (Gibco) and expanded through approximately 3 passages. These cells were re-designated as "PBS-1" cells and were again tested for adventitious or contaminating agents that could have entered the cells via source tissues, previous growth in bovine serum, or previous use of porcine trypsin (Table 2).

TABLE 2

Supplemental adventitious agents testing of PBS-1 Progenitor cells

| Agent | Test | Result |
| --- | --- | --- |
| Marek's disease | AGP | Negative |
| Viable bacteria/fungi | 9 CFR 113.26 | Negative |
| Extraneous bacteria/fungi | 9 CFR 113.27 | Negative |
| *Mycoplasma* | 9 CFR 113.28 | Negative |
| *Salmonella* | 9 CFR 113.30 | Negative |
| Avian lymphoid leukosis | 9 CFR 113.31 | Negative |
| Hemagglutinating viruses | 9 CFR 113.34 | Negative |
| Pathogens by chick embryo test | 9 CFR 113.37 | Negative |
| Cytopathic/hemadsorbing agents | 9 CFR 113.46 | Negative |
| Extraneous agents in MSV | 9 CFR 113.55 | Negative |

Because this testing was primarily for agents of veterinary origin, most tests were conducted according to 9 CFR.

PBS-1 cells shown to be free of common adventitious or contaminating agents (total passage from origin 309-310) were adapted to animal product-free growth through sequential replacement of complete DMEM medium with certified animal product free medium in the absence of any antibiotics (OptiPRO™ (a serum-free, animal origin-free culture medium), Gibco®). Cells were detached during this process only with a synthetic trypsin replacement (TrypLE Express, Gibco). This process required 7 total passages (approximately 14 doublings) to complete transition to animal product free growth conditions (FIG. 1). Cells were passed 1 additional time (total passage from origin 318 to 319) and aliquots stored under liquid nitrogen to provide a baseline for future genetic comparisons. The present invention includes these PBS-1 cells that were adapted to animal product free growth. These adapted cells have been designated as "PBS-12 SF" cells. PBS-12 SF cells have undergone a further 20 passages in animal product free conditions and several cloned derivatives are under expansion growth.

The PBS-12 SF cell line of the present invention has been shown to propagate Anhui/01/2005-PR8IBCDCRG-5, VNH5N1-PR8/CDC-RG, A/NewCaledonia/20/1999 and A/Wisconsin/67/2005 viruses. The method of the present invention can also be envisioned to support the replication of other viruses such as Adenoviridae, Arenaviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, Togaviridae. This list of viruses is not all inclusive and is only to serve as an example of the utility of the present invention.

In addition to the PBS-12 SF cell line, the invention also includes the cell line PBS-12 SF that has been infected with a virus, e.g., an animal or human virus such as those identified hereinabove. Further, the invention includes such an infected cell line wherein the virus is recombinant, e.g., one or more non-native genes have been inserted into the virus, one or more native genes have been deleted from the virus, or the viral genome is entirely contained within one or more plasmid vectors.

In one embodiment of the present invention, the PBS-12 SF cell line is used in virus isolation (VI) assays for the identification of any virus that may be an etiological agent in a diseased animal or human. A tissue, sputum, nasal swab, serum, or other sample from a diseased animal or human is inoculated onto tissue culture dishes containing a monolayer of PBS-12 SF cells. The inoculated PBS-12 SF cells are incubated and upon development of cytopathic effect (CPE) which is indicative of viral infection, the infected cells are used to prepare stocks of the inoculated virus to use for virus identification by infecting a plurality of PBS-12 SF cell monolayers and after development of CPE, reacting the infected PBS-12 SF monolayers with a panel of virus specific antibodies that are directly labeled to allow detection or by subsequently reacting with labeled antibodies specific for the first antibody. Alternatively, the inoculated PBS-12 SF monolayer is tested sequentially against a panel of virus-specific antibodies that are directly labeled to allow detection or by subsequently reacting with labeled antibodies specific for the first antibody.

In another embodiment of the present invention, the PBS-12 SF cell line is used to produce a vaccine. The cell line first is infected with a virus, e.g., an animal or human virus. The cells may be a monolayer in tissue culture dishes or a monolayer in a roller bottle, a culture in suspension, or a monolayer on microcarrier beads in a bioreactor. At the appropriate time after infection, the infected PBS-12 SF cells and/or culture media are harvested and used to prepare a live or inactivated vaccine against the infecting virus.

Preparation of live or inactivated vaccines containing an animal or human virus is well-known to those skilled in the art. More specifically, preparation of vaccines using the method of the present invention is performed by infecting the PBS-12 SF cell line with a virus. The monolayers may be formed on tissue culture dishes, roller bottles, stirred vessels (fermenters), or microcarrier systems. In addition there is a multiplicity of other systems suitable for culturing cells such as bioreactors, spinner cultures, or cubes. The media used to propagate the immortal cells may be any of the commonly available tissue culture media. However, the media may be serum-free or animal-product free. If desired, the media may contain antibiotics.

The preferred medium comprises commercially available OptiPRO™ SFM (a serum-free, animal origin-free culture medium; Invitrogen Corp.) The monolayer is inoculated with any animal or human virus. The virus may be an attenuated form of the virus adapted to replicate on CEF cells or attenuated virus adapted to replicate on PBS-12 SF cells or the cell line deposited as ATCC®-PTA-8565 (American Type Culture Collection). The culture fluid is harvested after the onset of cytopathic effect. The harvested culture fluid can be frozen, preferably after the addition of a stabilizer. Alternatively, the harvested culture fluid may be lyophilized, preferably in the presence of a stabilizer. The frozen or lyophilized virus may be diluted with culture medium to provide an appropriate dose of live virus vaccine. The vaccine may then be administered to an animal or human by any of a plurality of methods which include but are not limited to inoculation intramuscularly or subcutaneously, spraying, ocularly, nasally, orally, or in ovo.

Also, an inactivated vaccine may be prepared from the harvested culture fluid. Inactivation may be achieved by treating the virus by any of the methods commonly employed to make inactivated vaccines. These methods include but are not limited to formaldehyde treatment, betapropriolactone treatment, ethylene-imine treatment, treatment with a plurality of organic solvents, treatment with a plurality of detergents, treatment with gamma radiation or X-rays, or treatment with ultraviolet light. The methods recited herein serve as known examples for inactivating a virus.

Inactivated virus vaccines also may be administered to an animal or human and are usually administered mixed with an adjuvant such as aluminum hydroxide, and an emulsifier such as oil, or a detergent. The inactivated vaccine can be administered to the animal or human by any of a plurality of methods which include but are not limited to inoculation intramuscularly or subcutaneously, spraying, ocularly, nasally, orally, or in ovo.

Serum deprivation induces profound changes in cellular gene expression [6, 10, 20]. Serum provides numerous growth signals to cells, including those acting through serum response factor (SRF) [20], insulin, and insulin like growth factor, among others. In most cases, including parental PBS-1 cells, withdrawal of serum causes either quiescence (cessation of cell growth) or immediate activation of apoptotic pathways with subsequent cell death [6]. However, by slowly removing serum over a long period in culture and replacing it with a serum-free or animal product free growth medium, cells can become re-programmed to constitutively express genes that would normally not be expressed in the presence of serum or that can circumvent the normal growth inhibition due to serum withdrawal. While genetically, the parental cells (PBS-1) and serum free cells (PBS-12 SF) should appear similar, they may be very different either epigenetically (due to changes in DNA methylation and acetylation) or on a gene expression basis. Gene expression patterns of PBS-12SF cells and PBS-1 cells were compared using an AFFYMETRIX® Chicken GENECHIP® and it was found that greater than 300 genes were expressed at significantly different (>2-fold change; $p<0.001$) levels in PBS-12SF cells as compared to PBS-1 cells (data not shown).

Figure 2A:
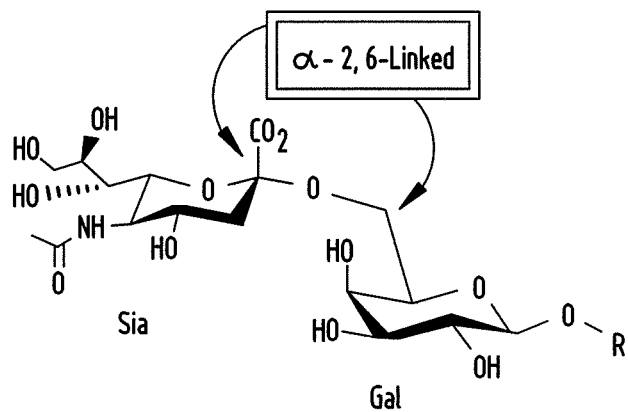
FIGS. 2A and 2B show the chemical structures of cell surface receptors with either a Sia2-6Gal or a Sia2-3Gal moiety, respectively.
Figure 2B:
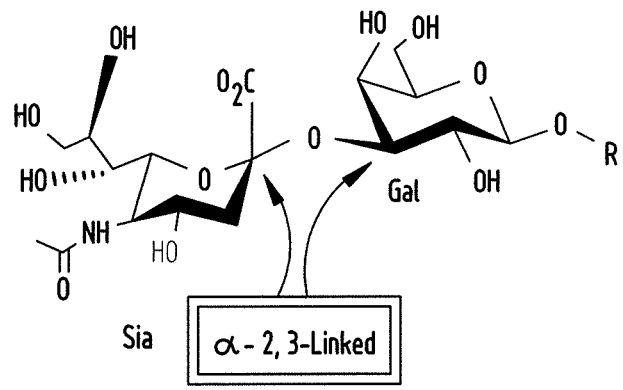

In view of the differential expression of viral cell surface receptors, the PBS-12 SF cell line appears to be different either epigenetically (due to changes in DNA methylation and acetylation) or on a gene expression basis as compared to the PBS-1 cell line. More specifically, influenza virus attachment to terminal sialyloligosaccharide receptor determinants of cell surface glycoproteins initiates influenza virus infection [4]. There are two major types of terminal sialyl-galactose moieties found in nature, which are Sia2-6Gal (FIG. 2A) and Sia2-3Gal (see, FIG. 2B). Human influenza viruses preferentially bind to cellular receptors containing a Sia2-6Gal linkage, whereas avian viruses preferentially bind to Sia2-3Gal receptors [3]. Hemagglutinin (HA) is a highly antigenic membrane glycoprotein that facilitates virion entry into the epithelial cells by attachment to sialic acid receptors containing the galactose linkages. It has been shown that isolating human influenza virus in embryonated eggs can result in amino acid substitutions in the area of the receptor binding site of the HA which are antigenically significant [12, 24, 25]. Because of this mutation, a strain which is being used for epidemiological and vaccine purposes may not offer complete protection against infection by the circulating influenza virus. Also, it has been shown that passaging mammalian influenza viruses in eggs can result in a change in the receptor specificity from Sia2-6Gal to avian Sia2-3Gal linkage [9]. Therefore, it is important that a cell line being used for vaccine production contains both receptors and does not replicate viruses with antigenically and structurally different HA molecules.

FACS analysis was performed to determine the expression of Sia2-3Gal and Sia2-6Gal moities on the surface of PBS-1, PBS-12SF, MDCK, CHO, and CEK cells (FIGS. 3A-3J). Although PBS-1 cells have been shown in these experiments to successfully replicate human influenza, only 11% of these cells bound to the SNA lectin, which is specific for Sia2-6Gal linkages preferred by human influenza. Surprisingly, 75% of PBS-12SF cells bound to the SNA lectin. This suggests that during the adaptation process from serum to serum-free conditions, the cells developed Sia2-6Gal-containing receptors in addition to Sia2-3Gal receptors. As expected, MDCK cells successfully bound to both MAA and SNA lectins, with percentages of 97 and 96 respectively. Receptor specificity is an important factor for influencing the susceptibility of cells to virus infection. If a proper sialic acid receptor is absent on a cell, the virus may be unable to bind to the cell surface and infect the cell. Also, if an influenza replication system consists of one predominant linkage, such as eggs with Sia2-3Gal, it can result in the change in the receptor specificity of the virus [9]. Therefore, it is very favorable that PBS12-SF cells contain both receptors.

In order to determine the quantity of influenza virus replication in vitro, two commonly used methods were used [17, 23]; the HA assay and the measurement of virus infectivity titers in culture supernatants. PBS-1, PBS-12SF, CEK, MDCK, and Vero cells were infected with reassortant H5N1 strains, Anhui/01/2005-PR8 IBCDC RG-5 and VNH5N1-PR8/CDC-RG to compare avian-human influenza A reassortant virus replication of cell supernatants. PBS-1 and CEK cells have previously been shown to successfully replicate influenza virus without the need for exogenous agents, such as trypsin. Because of this information, these cells were infected, along with PBS-12SF cells, with and without the addition of trypsin. MDCK and Vero cells require trypsin [14, 28], so these two cell lines were only infected in the presence of trypsin. Results show that PBS-1, PBS-12SF, and CEK cells replicated both strains with and without trypsin, although PBS-1 and PBS-12SF produced high titers with trypsin (Table 3). Table 3 shows Avian-human influenza A reassortant virus replication titers compared with cell supernatants of PBS-1, PBS-12SF, CEK, MDCK, and Vero cells.

TABLE 3

| | Strain | | | |
|---|---|---|---|---|
| | Anhui/01/2005-PR8IBCDCRG-5 | | VNH5N1-PR8/CDC-RG | |
| Cell line | $log_{10}TCID_{50}/ml$ | HAU/50 μl | $log_{10}TCID_{50}/ml$ | HAU/50 μl |
| PBS-1 cells with 1 μg/ml trypsin/without trypsin | 6.35/6.18 | 32/32 | 6.47/5.46 | 32/32 |
| PBS-12 SF cells with 1 μg/ml trypsin/without trypsin | 7.45/5.14 | 32/16 | 5.46/5.26 | 16/16 |
| CEK cells with 1 μg/ml trypsin/without trypsin | 4.96/5.64 | 32/32 | 4.17/5.78 | 16/32 |
| MDCK cells with 1 μg/ml trypsin | 7.30 | 64 | 6.48 | 512 |
| Vero cells with 1 μg/ml trypsin | 6.32 | 2 | 5.64 | 16 |

PBS-1, PBS-12SF, and CEK cells were tested with and without the presence of trypsin. All cell types were infected with influenza virus at an MOI of 0.1 and incubated until 50% cell death. The culture supernatants were initially diluted 1:10, and then a ½ log 10 dilution series was performed. They were reinfected on confluent MDCK cells for growth comparison. The wells were examined for presence of absence of CPE using microscopy. To confirm results, the culture supernatants were harvested and tested for HA activity to indicate if the cells in individual wells were infected.

The viral particle concentration of the supernatants remained rather consistent for all three cell types with values of 16-32 HAU/50 μl. Supernatants from MDCK cells demonstrated high growth titers for both strains infected which were comparable to PBS-1 cells and PBS-12SF cells with the addition of trypsin. The HAU/50 μl values were higher for MDCK supernatants, however, than PBS-1 and PBS-12SF. Vero cells did not replicate the two reassortant strains as successfully as PBS-1 and PBS12-SF supernatants, and their HA titers were lower as well. The Vero cells may have not replicated as well as the others because they have been show to rapidly destroy trypsin [13], and trypsin was only added before and after infection. Therefore, if trypsin would have been repeatedly added to the cells during infection, the titers may have been higher [7]. Due to increased costs and contamination risks from repeatedly adding trypsin, it is advantageous that PBS-1 and PBS 12-SF cells do not require this addition.

Since MDCK cells were capable of replicating these reassortant strains to comparable titers of PBS-1 and PBS-12SF cells, these two strains were adapted (in addition to human influenza strains A/NewCaledonia/20/1999 and A/Wisconsin/67/2005) to MCK, PBS-1, and PBS-12SF cells to determine if higher titers could be reached for PBS-1 and PBS-12SF cells. FIG. 4 demonstrates that at passages 1-3, the titer for most of the cell supernatants infected with the four influenza strains appears to be decreased. This is likely because the strains were still adjusting to the host cells. Increased titers generally occurred after passage 3, however, there were consistent fluctuations in titers. Because of this, these passages were used to calculate an average log 10TCID50/ml titer for the supernatants from each cell line. With the exception of Anhui/01/2005-PR8 IBCDC RG-5, PBS-1 and PBS-12SF cells produced higher influenza growth titers compared to MDCK cells. However, FIG. 5 demonstrates that MDCK cells produced the greatest amount of viral particles for all strains except A/Wisconsin/67/2005, which was determined through an HA assay.

Having now generally described the invention, the same will be more readily understood through reference to the following examples, which are provided by way of illustration, and are not intended to be limiting of the present invention, unless specified.

EXAMPLES

Example 1

PBS-1 Cell Adaptation to Serum Free Growth

To derive a serum free embryonic chick cell line, PBS-1 cells grown in Dulbeco's modified Eagle's medium supplemented with 10% fetal calf serum (complete DMEM) were transferred to medium consisting of 75% complete DMEM plus 25% of OptiPRO™ serum free medium (SFM) (see, FIG. 1). After one week of growth, the medium was replaced with a new mixture consisting of 50% complete DMEM and 50% OptiPRO™ SFM (a serum-free, animal origin-free culture medium). Following an additional week adaptation, cells were placed in medium consisting of 25% complete DMEM and 75% OptiPRO™ SFM (a serum-free, animal origin-free culture medium). After one week of adaptation, an attempt was made to place cells in 100% OptiPRO™ SFM (a serum-free, animal origin-free culture medium), however all cells in this culture died within 48 hours. Another group of cells that had been adapted to 75% OptiPRO™ SFM (a serum-free, animal origin-free culture medium) were transferred to 80% OptiPRO™ SFM (a serum-free, animal origin-free culture medium)/20% complete DMEM and the percentage of OptiPRO™ SFM (a serum-free, animal origin-free culture medium) increased in 10% increments over the next three weeks until the cells were in 100% OptiPRO™ SFM (a serum-free, animal origin-free culture medium). Cells were passed two additional times in 100% OptiPRO™ SFM (a serum-free, animal origin-free culture medium) prior to freezing aliquots at −135° C. The serum free cells were designated PBS-12SF and have now been passed up to 20 times in completely serum free (animal product free medium). During the entire process, only synthetic trypsin was used to dislodge the cells, thus avoiding any animal components in the growth or transfer process.

Example 2

Materials and Methods for Examples 3-5 Below

Cells

MDCK and Vero cell lines were obtained from the American Type Culture Collection (ATCC® (American Type Culture Collection), Manassas, Va.). Primary CEK cells were purchased from Charles River Laboratories (Boston, Mass.) and CHO cells were provided by Dr. George Smith (Michigan State University, East Lansing, Mich.). PBS-1 cells were derived and obtained as described previously [18]. PBS-1 cells were adapted to growth in serum free OptiPRO™-SFM (Gibco®, Invitrogen Life Technologies, Carlsbad, Calif.) supplemented with GlutaMAX-1 (40 mM concentration per liter of media, Gibco®) after 7 total passages and were renamed PBS-12SF. CHO cells were cultivated in DMEM/F-12 Media (Gibco®) containing 10% fetal bovine serum (FBS) (Gibco®), 100 IU/ml penicillin G, and 100 µl/ml streptomycin sulfate (Gibco®). MDCK, Vero, CEK and PBS-1 cell were cultivated using Dulbecco's Modified Eagle Medium (DMEM) (Gibco®) containing 10% FBS, 100 IU/ml penicillin G, and 100 µl/ml streptomycin sulfate.

Detection of Sia2-3Gal and Sia2-6Gal Moieties

Fluorescence-activated cell sorter (FACS) analysis of Sia2-3Gal and Sia2-6Gal moieties expression on the surface of PBS-1, PBS-12SF, MDCK, CHO, and CEK cells was performed as described previously [7, 8] using a digoxigenin glycan differentiation kit (Roche Applied Science, Mannheim, Germany). The cells were released from the culture flasks using trypsin. They were then washed once, resuspended in fresh media specific to each cell type as described above, and incubated for 1 hr at 36° C. to restore the trypsin-digested receptors. The cells were resuspended to $10^6$ cells/0.1 ml with phosphate buffered saline (PBS) and seeded into a 96-well round bottom plate. Aliquots of cells were incubated for 1 hr at room temperature with DIG-labeled lectins *Sambucus nigra* agglutinin (SNA) (specific for Sia2-6Gal) or *Maackia amurensis* agglutinin (MAA) (specific for Sia2-3Gal). Control cells were incubated without lectins. The cells were washed three times with PBS and were then incubated with anti-digoxigenin-fluorescein Fab fragments (Roche Applied Science) for 1 hr at room temperature. After three washes, the cells were analyzed for fluorescence intensity on a BD FACSCalibur flow cytometer using CellQuest Pro Software (Becton Dickinson, San Jose, Calif.).

Viruses

Human influenza virus strains A/NewCaledonia/20/1999 (H1N1) and A/Wisconsin/67/2005 (H3N2) and reassortant vaccine viruses Anhui/01/2005-PR8 IBCDC RG-5 and VNH5N1-PR8/CDC-RG were generously provided by the Centers for Disease Control and Prevention (CDC, Atlanta, Ga.).

Virus Infection and Propagation

PBS-1, PBS-12SF, Vero, MDCK, and CEK cells were cultured in growth media described above in 12 well plates for 24 hrs (density of $1.0\times10^4$ cells per cm2 for PBS-1, PBS-12SF, and Vero cells, $7.8\times10^4$ cells per cm2 for MDCK cells, and $3.1\times10^4$ cells per cm2 for CE cells). Once the cells reached 80% confluency (24 hrs), they were washed with infection medium and inoculated with 100.mu.l volumes of virus, giving multiplicities of infection (MOI) of 1:10 (one virus per 10 cells). Each plate also contained an uninfected well of each cell type as control. The infection medium for PBS-1, Vero, MDCK, and CEK cells consisted of DMEM with 0.2% BSA, 25 mM HEPES, and 1.0 µg/ml tosyl phenylalanyl chloromethyl ketone (TPCK)-treated trypsin (Gibco®). Infection medium for PBS-12SF cells consisted of OptiPRO™ SFM (a serum-free, animal origin-free culture medium) supplemented with 0.2% BSA, 25 mM HEPES, and 1.0 µg/ml TPCK-treated trypsin. The inoculated cell cultures were placed in an incubator at 37° C. for 1 hr. After 1 hr, the media was removed, rinsed, and 1 ml of fresh infection media was added. The cells were incubated until they reached 50% death, which generally occurred within 1-3 days of infection. The supernatants were centrifuged for 15 min at 300×g to remove cell debris. HA assays and titer measurements were performed on all supernatants to determine virus yield as described below.

Hemagglutination Assay

The HA assay was performed by serially diluting 50 µl of culture supernatants 2-fold with PBS in V-bottom plates. Subsequently, 50 µl of 1% chicken red blood cells (Innovative Research, Inc., Southfield, Mich.) were added to each well. The plates were incubated for 1 hr at room temperature and the HA patterns were determined visually.

Virus Infectivity Assay

The culture supernatants were tested for the presence of virus infectivity as previously described [27]. Titration of infectious virus was performed on MDCK cells for the first two passages. Starting on the third passage, the titrations were performed on the corresponding cell line in which the virus was infected. Cells were seeded in 96 well plates at densities of $5.9\times10^4$ cells/cm2 for MDCK cells or $9.4\times10^4$ cells/cm2 for PBS-1 and PBS-12SF cells and grown at 37° C. for 24 hr in a 5% CO2 incubator. Once confluency was obtained, the growth medium was removed and the cells were washed two times with infection medium. The culture supernatants were initially diluted 1:10, and then a 10-fold dilution series was performed using infection media specific for each cell type. The final volume of each well was 100 µl and the plates were incubated for 2 hr at 37° C. After incubation, the inoculum was removed, the plates were washed, and 200 µl of fresh infection medium was added to all wells. The infected cultures were incubated for 72 hr at 37° C. The wells were examined for presence or absence of CPE using microscopy. To confirm results, the culture supernatants were harvested and tested for HA activity to indicate if the cells in individual wells were infected. The 50% tissue culture infective dose (TCID50) was determined via the Reed and Muench method [22].

Example 3

Detection of Sia2-3Gal and Sia2-6Gal Moieties

BD FACSCalibur flow cytometer and CellQuest Pro Software were used to investigate the presence of the Sia2-3Gal and Sia2-6Gal linkages. The MAA lectin was specific for Sia2-3Gal linkages and the SNA lectin was specific for Sia2-6Gal linkages. The controls for PBS-1, PBS-12SF, CEK, MDCK, and CHO were populations of cells that were only stained with anti-digoxigenin-fluorescein Fab fragments, which are shown as the unshaded profiles in FIG. 3A-3H. In addition to serving as a positive control for MAA binding to Sia2-6Gal moieties (88% of cells bound), CHO cells also served as controls to establish background binding of SNA, since these cells do not contain any Sia2-3Gal moieties (FIGS. 3A and 3B). MAA bound strongly to the surface of PBS-1 cells (84% of cells), whereas SNA did not bind at levels above background (FIGS. 3C and 3D). In contrast, PBS-12SF cells efficiently bound to both MAA (94%) and SNA (75%) (FIGS. 3E and 3F). This indicates that the cell surface influenza receptors on PBS-1 and PBS-12SF cells are very different and that PBS-12SF cells contain receptors for both human and avian influenzas. As expected, MDCK cells bound efficiently to both lectins (MAA=97%; SNA=96%; FIGS. 3G and 3H).

Example 4

Comparing Avian-Human Influenza A Reassortant Virus Replication of Cell Supernatants PBS-1, PBS-12SF, and CEK cells were infected with reassortant vaccine viruses Anhui/01/2005-PR8 IBCDC RG-5 and VNH5N1-PR8/CDC-RG with and without the addition of trypsin. MDCK and Vero cells were infected with the same two strains but only in the presence of trypsin, since they require trypsin for efficient growth of the influenza viruses on the cells. Results in Table 3 demonstrate that PBS-1 and PBS-12SF cells had greater virus titers compared to CEK cells for Anhui/01/2005-PR8 IBCDC RG-5 with the addition of 1.0 µg/ml trypsin. When trypsin was not added to the infection media, this strain grew slightly more effectively on CEK cells, although only by a log 10TCID50/ml value of 0.50-0.65 greater. The HA units remained rather consistent for these three cell types with and without the addition of trypsin, ranging from an HAU/50 µL of 16-32. MDCK cells were capable of replicating this Anhui/01/2005-PR8 IBCDC RG-5 to a log 10TCID50/ml titer of 7.30, which is slightly less than the infection on PBS-12SF cells with trypsin (titer of 7.45). The titer from MDCK cells was, however, greater than that of PBS-1 cells with trypsin, which produced a titer of 6.35. MDCK supernatant had a slightly higher HA concentration than the rest, with an HAU/50 µL value of 64 compared to 16-32 from the other cell types for the Anhui/01/2005-PR8 IBCDC RG-5 strain. Vero cells replicated this strain at a comparable titer to PBS-1 cells with trypsin (6.32 and 6.35 respectively). However, this strain replicated most successfully in PBS12-SF cells in the presence of trypsin, yielding a titer of 7.45. Additionally, the supernatant from Vero cells contained a low concentration of HA compared to the other cells, at a HAU/50 µL of 2. Similarly to Anhui/01/2005-PR8 IBCDC RG-5, the reassortant strain VNH5N1-PR8/CDC-RG more successfully replicated on PBS-1 and PBS-12SF cells with the addition of 1.0 µg/ml trypsin than without trypsin. This strain also replicated better on CEK cells in the absence of trypsin. PBS-1 cells with trypsin replicated this strain better than the other cell types, with a log 10TCID50/ml titer of 6.47 compared to 5.46 and 4.17 for PBS-12SF and CEK cells, respectively. PBS-1 cells also contained the greatest amount of HA particles, with an HAU/50 µL value of 32 compared to 16 for the other two cell types. MDCK cells replicated this strain to a titer of 6.48, which is extremely close to PBS-1 cells with trypsin. However, the supernatant from the MDCK cells contained an extremely high concentration of HA particles with an HAU/50 µL value of 512. Supernatant from Vero cells produced a titer of 5.64 and an HAU/50 µL value of 16.

Example 5

Adaptation of Influenza Viruses to Host Cells

Figure 5:
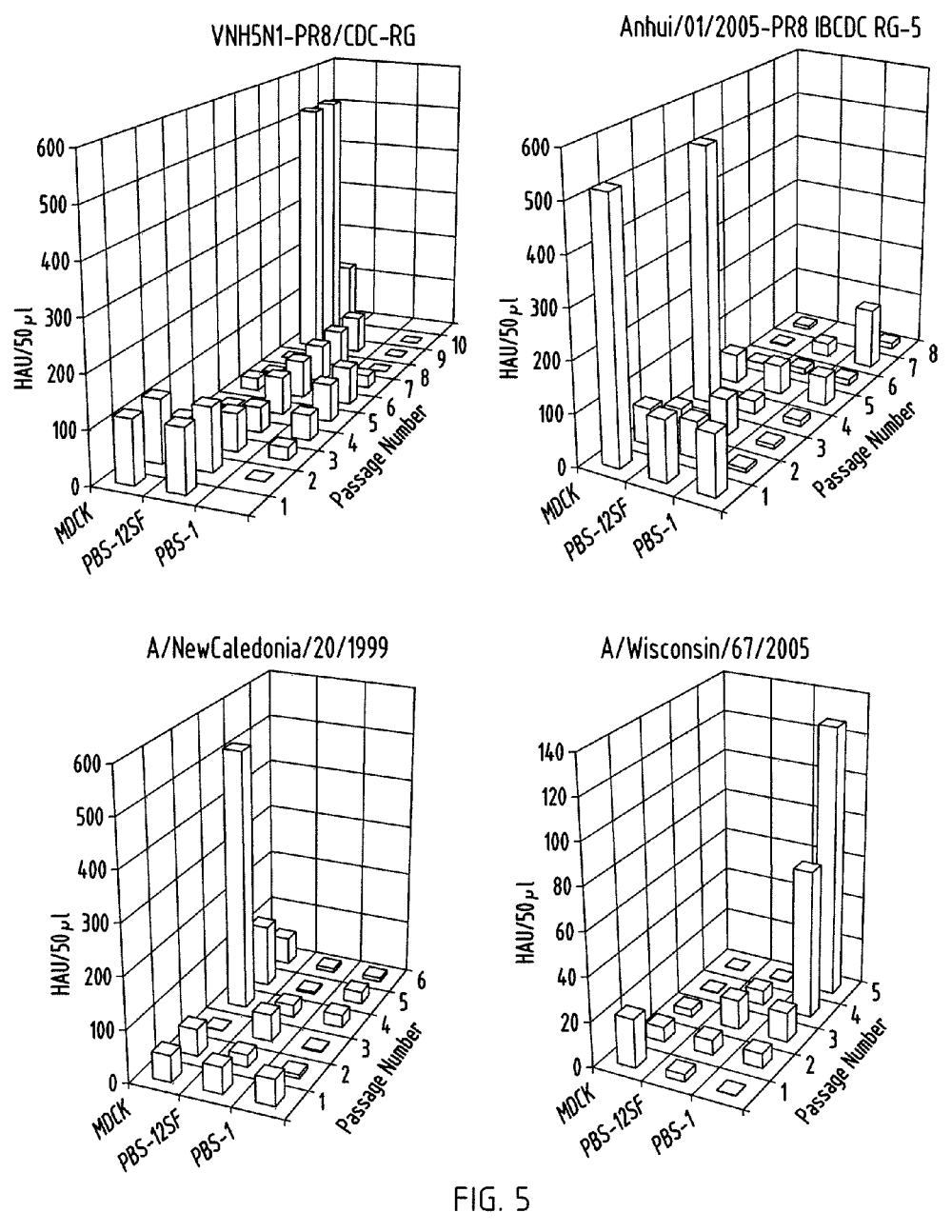

In efforts to increase the titers of influenza virus from the previous infection, the influenza viruses were adapted to the host cells. MDCK, PBS-12SF, and PBS-1 cells were tested and they were all supplemented with 1.0 µg/ml trypsin. The same two reassortant strains were tested, Anhui/01/2005-PR8 IBCDC RG-5 and VNH5N1-PR8/CDC-RG, in addition to two human influenza strains, A/NewCaledonia/20/1999 (H1N1) and A/Wisconsin/67/2005 (H3N2). Although an increase in growth titer was predicted as the cells adapted to the host cells, FIG. 4 shows that this did not occur. However, using these results, the average titer produced from these host cells can be determined after a series of passages as well as the standard deviation. Results from MDCK infection with strain VNH5N1-PR8/CDC-RG show the growth titers were greatest at passage 1, with a log 10TCID50/ml value of 7.27. PBS-12SF cells infected with the strain showed greatest titers at passage 1, with a titer of 7.27 while PBS-1 supernatants demonstrated the highest titer at passage 5 (7.52). The average log 10TCID50/ml titers for this strain infected on MDCK, PBS-12SF, and PBS-1 cells were 4.38±1.93, 5.64±1.27, and 5.78±1.12 and HAU/50 µL of 147, 57, and 37 respectively (FIG. 5). MDCK supernatants from the Anhui/01/2005-PR8 IBCDC RG-5 infection reached highest titers at passages 1,9, and 10 (9.5). PBS-12SF supernatants from this infection demonstrated the highest titer at passage 1 (7.77), and PBS-1 cells reached highest titer at passage 4 (8.52). The average log 10TCID50/ml titers for this strain infected on MDCK, PBS-12SF, and PBS-1 cells were 6.10±2.49, 5.81±1.76, and 4.88±2.68 and HAU/50 µL of 137, 75, and 23 respectively. MDCK supernatants containing A/NewCaledonia/20/1999 (H1N1) reached a significant titer peak at passage 4 with a titer of 8.27, while PBS-12SF supernatants infected with this strain replicated most successfully at passages 4 and 6 (8.52). PBS-1 cells also reached the highest titer at passage 4 (9.53). The average supernatant titers for the A/NewCaledonia/20/1999 strain were 5.01±2.08, 7.10±1.69, and 6.68±1.65 and HAU/50 µL of 139, 36, and 27 for MDCK, PBS-12SF, and PBS-1 cells respectively. The last strain tested, A/Wisconsin/67/2005, replicated best on MDCK cells on the first passage, with a titer of 8.02. PBS-12SF cells were most successful at replicating this strain on the fifth passage and yielded a titer of 6.77. PBS-1 supernatants demonstrated the highest titers at the fourth passage, with a titer of 9.28. The average titers of the supernatants infected with A/Wisconsin/67/2005 for MDCK, PBS-12SF, and PBS-1 cells were 2.61±3.72, 5.16±1.06, and 6.41±2.75 and HAU/50 µL of 9, 7, and 43 respectively. In addition to measuring the infectivity of the supernatants, the number of virus particles present was also measured via the HA assay. These results show that for strains VNH5N1-PR8/CDC-RG, Anhui/01/2005-PR8 IBCDC RG-5, and A/NewCaledonia/20/1999, MDCK cells produced the greatest number of viral particles (H1N1) and PBS-12SF produced the greatest number of particles for A/Wisconsin/67/2005.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

REFERENCES

1. Abujoub, A. and P. M. Coussens, Development of a sustainable chick cell line infected with Marek's disease virus. Virology, 1995. 214(2): p. 541-9.

2. Abujoub, A. A. and P. M. Coussens, Evidence that Marek's disease virus exists in a latent state in a sustainable fibroblast cell line. Virology, 1997. 229(2): p. 309-21.
3. Bardiya N, Bae J H. Influenza vaccines: recent advances in production technologies. Applied microbiology and biotechnology 2005; 67(3):299-305.
4. Gambaryan A S, Robertson J S, Matrosovich M N. Effects of egg-adaptation on the receptor-binding properties of human influenza A and B viruses. Virology 1999; 258(2): 232-9.
5. Genzel Y, Fischer M, Reichl U. Serum-free influenza virus production avoiding washing steps and medium exchange in large-scale microcarrier culture. Vaccine 2006; 24(16): 3261-72.
6. Gos, M., J. Miloszewska, et al., Cellular quiescence induced by contact inhibition or serum withdrawal in C3H10T1/2 cells. Cell Prolif, 2005. 38(2): p. 107-16.
7. Govorkova E A, Murti G, Meignier B, de Taisne C, Webster R G. African green monkey kidney (Vero) cells provide an alternative host cell system for influenza A and B viruses. Journal of virology 1996; 70(8):5519-24.
8. Govorkova E A, Matrosovich M N, Tuzikov A B, Bovin N V, Gerdil C, Fanget B, et al. Selection of receptor-binding variants of human influenza A and B viruses in baby hamster kidney cells. Virology 1999; 262(1):31-8.
9. Ito T, Suzuki Y, Takada A, Kawamoto A, Otsuki K, Masuda H, et al. Differences in sialic acid-galactose linkages in the chicken egg amnion and allantois influence human influenza virus receptor specificity and variant selection. Journal of virology 1997; 71(4):3357-62.
10. Iyer, V. R., M. B. Eisen, et al., The transcriptional program in the response of human fibroblasts to serum. Science, 1999. 283(5398): p. 83-7.
11. Katz, J. M. and R. G. Webster, Amino acid sequence identity between the HA1 of influenza A (H3N2) viruses grown in mammalian and primary chick kidney cells. J Gen Virol, 1992. 73 (Pt 5): p. 1159-65.
12. Katz J M, Webster R G. Antigenic and structural characterization of multiple subpopulations of H3N2 influenza virus from an individual. Virology 1988; 165(2):446-56.
13. Kaverin N V, Webster R G. Impairment of multicycle influenza virus growth in Vero (WHO) cells by loss of trypsin activity. Journal of virology 1995; 69(4):2700-3.
14. Kistner O, Barrett P N, Mundt W, Reiter M, Schober-Bendixen S, Dorner F. Development of a mammalian cell (Vero) derived candidate influenza virus vaccine. Vaccine 1998; 16(9-10):960-8.
15. Lavrentieva, I. N., T. E. Medvedeva, and D. B. Golubev, Characterization of the reproduction of influenza A epidemic viruses in cell cultures. Acta Virol, 1986. 30(2): p. 137-42.
16. Lee E U, Roth J, Paulson J C. Alteration of terminal glycosylation sequences on N-linked oligosaccharides of Chinese hamster ovary cells by expression of beta-galactoside alpha 2,6-sialyltransferase. The Journal of biological chemistry 1989; 264(23):13848-55.
17. Masurel N, Ophof P, de Jong P. Antibody response to immunization with influenza A/USSR/77 (H1N1) virus in young individuals primed or unprimed for A/New Jersey/76 (H1N1) virus. The Journal of hygiene 1981; 87(2):201-9.
18. Ogura H, Fujiwara T. Establishment and characterization of a virus-free chick cell line. Acta medica Okayama 1987; 41(3):141-3.
19. Pau M G, Ophorst C, Koldijk M H, Schouten G, Mehtali M, Uytdehaag F. The human cell line PER.C6 provides a new manufacturing system for the production of influenza vaccines. Vaccine 2001; 19(17-19):2716-21.
20. Pochampally, R. R., J. R. Smith, et al., Serum deprivation of human marrow stromal cells (hMSCs) selects for a subpopulation of early progenitor cells with enhanced expression of OCT-4 and other embryonic genes. Blood, 2004. 103(5): p. 1647-52.
21. Poland, G. A., R. M. Jacobson, and P. V. Targonski, *Avian and pandemic influenza: An overview*. accine, 2007. 25(16): p. 3057-3061.
22. Reed L J, Muench H. A simple method of estimating fifty percent endpoints. Am J Hyg 1937; 27(3):493-7.
23. Rimmelzwaan G F, Baars M, Claas E C, Osterhaus A D. Comparison of RNA hybridization, hemagglutination assay, titration of infectious virus and immunofluorescence as methods for monitoring influenza virus replication in vitro. Journal of virological methods 1998; 74(1):57-66.
24. Robertson J S, Bootman J S, Newman R, Oxford J S, Daniels R S, Webster R G, et al. Structural changes in the haemagglutinin which accompany egg adaptation of an influenza A(H1N1) virus. Virology 1987; 160(1):31-7.
25. Schild G C, Oxford J S, de Jong J C, Webster R G. Evidence for host-cell selection of influenza virus antigenic variants. Nature 1983; 303(5919):706-9.
26. Selvaraj, A. and R. Prywes, Expression profiling of serum inducible genes identifies a subset of SRF target genes that are MKL dependent. BMC Mol Biol, 2004. 5: p. 13.
27. Szretter K J, Balish A L, Katz J M. Orthomyxoviruses; Influenza: Propagation, Quantification, and Storage. Current Protocols in Microbiology 2006:p. 15G.1.1-.G.1.22.
28. Tree J A, Richardson C, Fooks A R, Clegg J C, Looby D. Comparison of large-scale mammalian cell culture systems with egg culture for the production of influenza virus A vaccine strains. Vaccine 2001; 19(25-26):3444-50.
29. Wood, J. M., D. Major, et al., Preparation of vaccines against H5N1 influenza. Vaccine, 2002. 20 Suppl 2: p. S84-7.
30. Wood, J. M. and J. S. Robertson, Reference viruses for seasonal and pandemic influenza vaccine preparation. Influenza and Other Respiratory Viruses, 2006. 1: p. 5-9.

What is claimed is:

1. An isolated cell line designated PBS-12 SF which is deposited with the American Type Culture Collection with Accession Number PTA-8565.

2. The isolated cell line of claim 1, which is infected with a virus.

3. The isolated cell line of claim 2, wherein the virus is selected from the group of virus families consisting of Adenoviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, and Togaviridae.

4. The isolated cell line of claim 2, wherein the virus is capable of use in the preparation of a composition which renders an immune response to the virus.

5. The isolated cell line of claim 2, wherein the virus is recombinant.

6. The isolated cell line of claim 5, wherein one or more foreign genes have been inserted into the virus.

7. The isolated cell line of claim 5, wherein one or more genes have been deleted from the virus.

8. The isolated cell line of claim 2, wherein the cell line produces infectious virus when the cell culture is sub-confluent or confluent.

9. The isolated cell line of claim 1, wherein the cell line is capable of growing in a suspension.

10. A method of producing an immunogenic composition comprising the steps of providing the isolated cell line of claim 1; infecting the cell line with a virus; cultivating the cell line infected with the virus; and harvesting the virus from the cell line.

11. The method of claim 10, wherein the virus is selected from the group of virus families consisting of Adenoviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, and Togaviridae.

12. The method of claim 10, further comprising the step of inactivating the virus.

13. A method of producing an immunogenic composition comprising the steps of providing the isolated cell line of claim 1; transfecting the cell line with a clone containing a viral genome; cultivating the transfected cell line; and harvesting the virus from the cell line.

14. A method of producing an immunogenic composition comprising the steps of providing the isolated cell line of claim 1; transfecting the cell line with a plasmid containing a viral genome; cultivating the transfected cell line; and harvesting the virus from the cell line.

15. A method of administering an immunogenic composition to an animal or a human, comprising the steps of: providing the inactivated virus produced according to the method of claim 12 as an immunogenic composition; and inoculating an animal or human with the immunogenic composition.

16. The method of claim 15, wherein the inactivated virus is from a virus family selected from the group of virus families consisting of Adenoviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, and Togaviridae.

17. The method of claim 15, wherein an animal is inoculated with the immunogenic composition.

18. The method of claim 15, wherein a human is inoculated with the immunogenic composition.

19. A method for identifying a virus, comprising: (a) providing the isolated cell line of claim 1; (b) infecting said cell line with a virus; (c) cultivating the infected cell line to produce the virus; (d) reacting said infected cell line with an antibody or other reagent specific for the virus; and (e) visualizing infected cells reacted with the antibody or reagent.

20. The method according to claim 19, wherein the virus is selected from the group of virus families consisting of Adenoviridae, Birnaviridae, Coronaviridae, Flaviviridae, Herpesviridae, Orthomyxoviridae, Paramyxoviridae, Picornaviridae, Polyomaviridae, Poxviridae, Reoviridae, Retroviridae, Rhabdoviridae, and Togaviridae.

* * * * *

UNITED STATES PATENT AND TRADEMARK OFFICE
CERTIFICATE OF CORRECTION

PATENT NO.         : 8,716,016 B2                                Page 1 of 1
APPLICATION NO.    : 12/989261
DATED              : May 6, 2014
INVENTOR(S)        : Coussens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 357 days.

Signed and Sealed this

Twenty-ninth Day of September, 2015

Michelle K. Lee
*Director of the United States Patent and Trademark Office*